United States Patent [19]

Brush et al.

[11] 4,255,445

[45] Mar. 10, 1981

[54] 8-HYDROXY-6,7-(2-METHYL-2,3-DIHYDROFURO)-1-PHENYL-2,3,4,5-TETRAHYDRO-1H-3-BENZAZEPINES

[75] Inventors: Charles K. Brush, Malvern; Joseph Weinstock, Phoenixville, both of Pa.

[73] Assignee: SmithKline Corporation, Philadelphia, Pa.

[21] Appl. No.: 128,009

[22] Filed: Mar. 7, 1980

[51] Int. Cl.$^3$ .................. A61K 31/55; C07D 491/048
[52] U.S. Cl. ................................. 424/285; 260/346.71
[58] Field of Search .................... 260/346.71; 424/285

[56] References Cited

U.S. PATENT DOCUMENTS 4,105,785  8/1978  Mauvernay et al. ............ 260/346.71

*Primary Examiner*—Henry R. Jiles
*Assistant Examiner*—Bernard Dentz
*Attorney, Agent, or Firm*—William H. Edgerton; Richard D. Foggio; Alan D. Lourie

[57] ABSTRACT

8-Hydroxy-6,7-(2,3-dihydrofuro)-1-phenyl-2,3,4,5-tetrahydro-1H-3-benzazepines are prepared by a reaction sequence whose key is a dual cyclization forming the 3-benzazepine ring and fused thereto a dihydrofuran.

9 Claims, No Drawings

8-HYDROXY-6,7-(2-METHYL-2,3-DIHYDROFURO)-1-PHENYL-2,3,4,5-TETRAHYDRO-1H-3-BENZAZEPINES

This invention comprises a group of new chemical compounds whose structures comprise a 2,3,4,5-tetrahydro-1H-3-benzazepine skeleton substituted at 1 by a phenyl or substituted phenyl, at 6,7 by a condensed dihydrofuro ring and at 8 by a hydroxy. These compounds are, therefore, 8-hydroxy-6,7-(2-methyl-2,3-dihydrofuro)-1-phenyl-2,3,4,5-tetrahydro-1H-3-benzazepines. They have peripheral dopaminergic activity particularly renal vasodilating activity.

The compounds of this invention are represented by the following structural formula:

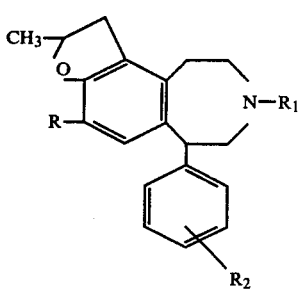

in which R is hydroxy or methoxy, $R_1$ is hydrogen, methyl or allyl and $R_2$ is hydrogen, methoxy, hydroxy, methylthio, methyl, trifluoromethyl or halo such as fluoro, chloro, bromo or iodo.

A sub-group of this invention comprises the compounds of Formula I in which R and $R_2$ are both hydroxy.

The pharmaceutically acceptable acid addition salts having the utility of the free bases of Formula I, prepared by methods well known to the art, are formed with both inorganic or organic acids, for example: maleic, fumaric, benzoic, ascorbic, pamoic, succinic, bismethylenesalicylic, methane sulfonic, ethane disulfonic, acetic, oxalic, propionic, tartaric, salicylic, citric, gluconic, aspartic, stearic, palmitic, itaconic, glycolic, p-aminobenzoic, glutamic, benzene sulfonic, hydrochloric, hydrobromic, sulfuric, cyclohexylsulfamic, phosphoric and nitric acids. The hydrohalic and especially methanesulfonic acid salts are of particular utility.

Also included in this invention are O-lower alkanoyl esters of the compounds of Formula I having from 2-8 carbon atoms in each alkanoyl group such as acetyl, isobutyryl, propionyl, isovaleryl, n-heptanoyl and others. When more than one hydroxy substituent is present it is more convenient to have the same alkanoyl group present at each position. The ester derivatives are prepared by treating the hydroxy parent of Formula I protected if necessary at position 3 by a N-benzyl substituent or by an acid addition salt with either a stoichiometric amount or a slight excess of an acyl halide or anhydride in the presence of an organic base optionally in an organic solvent.

It will be obvious to one skilled in the art that the compounds of Formula I may be present as diastereoisomers which may be resolved into d, l optical isomers. Resolution of the optical isomers may be conveniently accomplished by fractional crystallization of their salts with optically active acids from appropriate solvents. Specific methods of resolution useful for 3-benzazepines are disclosed in Swiss Pat. No. 555,831. Unless otherwise specified herein or in the claims, it is intended to include all isomers, whether separated or mixtures thereof. Where isomers are separated, the desired pharmacological activity will usually predominate in one of the isomers. However usually the mixture of isomers is used for the purpose of this invention.

The compounds of this invention are prepared by the following reaction sequence:

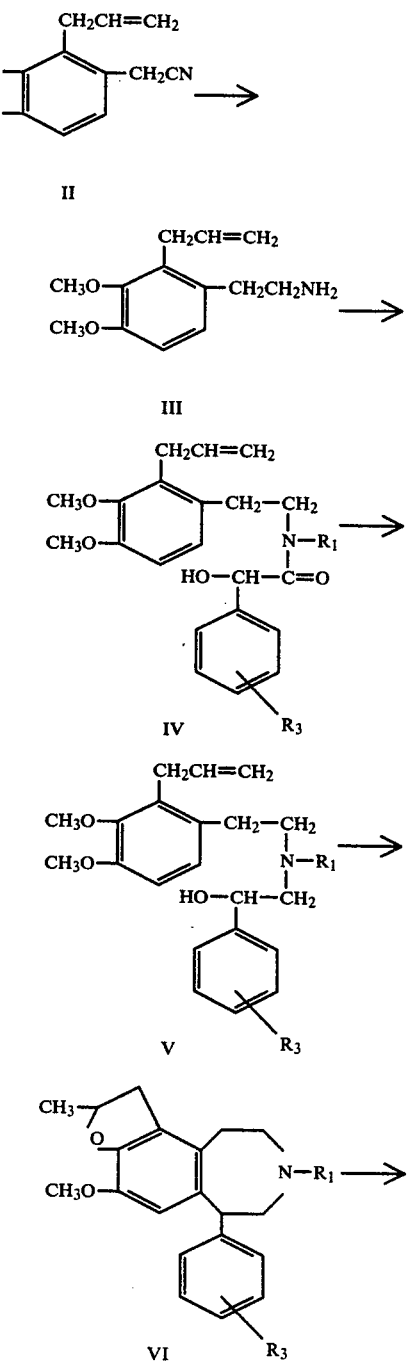

-continued

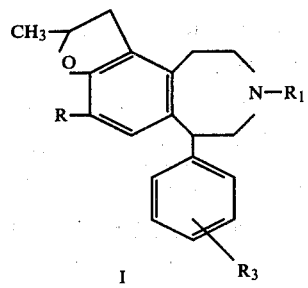

In the above flow diagram R and $R_1$ are as defined above for Formula I. $R_3$ is also as defined but should not be hydroxy.

2-Allyl-3,4-dimethoxyphenylacetonitrile (II) is prepared by reacting a known 2-allyl-3,4-dimethoxybenzyl halide with an alkali metal cyanide in an inert, dipolar aprotic solvent with heat. The resulting phenylacetonitrile is reduced using any specific nitrile reducing agent which does not act on the allyl group such as aluminum hydride in tetrahydrofuran at ambient temperature to give 2-allyl-3,4-dimethoxy-$\beta$-phenethylamine (III). Other catalyst are lithium aluminum hydride in tetrahydrofuran, triethyllithiumborohydride, or sodium bis(2-methoxyethoxy)-aluminum hydride. The amine is condensed with an optionally substituted methyl or ethyl mandelate, most conveniently by heating on a steam bath without solvent for 6-12 hours, to give an optionally substituted N-[2-(2-allyl-3,4-dimethoxyphenyl)ethyl]mandelamide (IV). The amide is then reduced using a specific amide reducing agent known to the art such as lithium aluminum hydride or especially sodium bis(2-methoxyethoxy)-aluminum hydride in a benzenoid solvent such as benzene, toluene or xylene or tetrahydrofuran at reflux temperature to give an optionally substituted N-(2-hydroxy-2-phenylethyl)-N-[2-(2-allyl-3,4-dimethoxyphenyl)ethyl]-amine (V). As an alternative to the mandelamide route to the secondary amine (V) the phenethylamine (III) may be reacted with the appropriate styrene oxide with heat at 90°–110° for from 1-3 hours.

The key reaction of the reaction sequence is the double cyclization of the secondary amine (V) to form the benzazepine and furan rings (V→VI). Good yields are realized from reacting the secondary amine (V) in the presence of sulfuric acid-trifluoroacetic acid at ambient temperature until the reaction is complete. Alternatively other cyclizing agents known to the art may be used such as hydrohalic acids such as 48% hydrobromic acid at 100° or hydriodic acid at reflux. Of course such hydrohalic acid cyclization will also split any methoxy substituents such as at 8 or on the 1-phenyl ring and thereby give a mixture of products which may be separated by standard isolation methods. In general the use of mild reaction conditions is preferred to minimize side reactions.

The 8-methoxy-6,7-(2-methyl-2,3-dihydrofuro)-1-phenyl-2,3,4,5-tetrahydro-1H-3-benzazepines of Formula VI are of prime use as intermediates. For example, they may be demethylated by reaction with boron tribromide or hydrobromic acid to give the hydroxylated products of Formula I.

Also the compounds of Formula VI in which $R_1$ is hydrogen may be N-alkylated by reactions standard in the art such as using allyl chloride, bromide or iodide as well as methyl iodide in an inert organic solvent such as acetonitrile in the presence of a tertiary organic base such as triethylamine, pyridine or dimethylaniline. The N-alkylated compounds are then demethylated as described above to give the compounds of Formula I in which $R_1$ is methyl or allyl.

The compounds of this invention have peripheral dopaminergic activity as measured by monitoring mean arterial blood pressure (MAP), mean renal blood flow (RBF), renal vascular resistance (RVR) and heart rate (HR) in the normal anesthetized dog. For example 6,7-(2-methyl-2,3-dihydrofuro)-8-hydroxy-1-(4-hydroxyphenyl)-2,3,4,5-tetrahydro-1H-3-benzazepine hydrobromide (A) gave the following results:

| Compound | Dose | | % Change | | |
|---|---|---|---|---|---|
| | µg/kg/min | MAP | RBF | RVR | HR |
| dopamine | 3 | −6.4* | +17.8* | −19.9* | −9.1* |
| A | 3 | 0 | +3.9 | −4.2 | 0 |
| | 30 | −3.3 | +7.4* | −9.4* | 0 |
| | 300 | −6.0* | +3.4 | −9.2* | −12.9* |

*significant for 2 dogs

The data demonstrate increased renal blood flow and decreased renal vascular resistance at 30 µg/kg/min. This result is an indication of peripheral dopaminergic activity and resultant improvement in cardiovascular function.

The same compound did not demonstrate significant central dopaminergic activity in the rotation test in lesioned rats at 10.0 mgm/kg intraperitoneally which is a standard test for anti-parkinsonism activity.

The pharmaceutical compositions of this invention having antihypertensive activity more especially peripheral dopaminergic activity are prepared in conventional dosage unit forms by incorporating a compound of Formula I, an isomer or a pharmaceutically acceptable acid addition salt or ester derivative thereof, with a nontoxic pharmaceutical carrier according to accepted procedures in a nontoxic amount sufficient to produce the desired pharmacodynamic activity in a subject, animal or human. Preferably the compositions will contain the active ingredient in an active but nontoxic amount selected from about 50 mg to about 500 mg. preferably about 75-250 mg of active ingredient per dosage unit but this quantity depends on the relative potency of the basic compound, the specific biological activity desired, the route of administration, oral or parenteral, and the condition of the patient.

The pharmaceutical carrier employed may be, for example, either a solid or liquid. Exemplary of solid carriers are lactose, terra alba, sucrose, talc, gelatin, agar, pectin, acacia, magnesium stearate, stearic acid, and the like. Exemplary of liquid carriers are isotonic saline for parenteral use or syrup, peanut oil, olive oil, water and the like for soft gelatin capsules. Similarly the carrier or diluent may include any time delay material well known to the art, such as glyceryl monostearate or glyceryl distearate alone or with a wax. Such sustained release products as well as derivatives which may be gradually metabolized to the active parent can be employed to prolong the unique biological activity of the compounds of this invention.

A wide variety of pharmaceutical forms can be employed. Thus, if a solid carrier for oral administration is used the preparation can be tableted, placed in a hard gelatin capsule in powder, regular or sustained release pellet form, or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable liquid such as an ampul, or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to give the desired end product.

The method of producing peripheral dopaminergic activity in accordance with this invention comprises administering orally or parenterally to a subject in need of such activity a compound of Formula I or a pharmaceutically acceptable acid addition salt thereof, usually combined with a pharmaceutical carrier, in a nontoxic amount sufficient to produce said activity as described above. The route of administration may be any route which effectively transports the active compound to the peripheral dopamine receptors which are to be stimulated such as orally or parenterally, the oral route being preferred. Advantageously, equal oral doses within the ranges given above will be administered several times, such as from two to five times, a day, with the daily dosage regimen being selected from about 50 mg to about 1.0 g., preferably 75–500 mg/kg for oral dosage units. When the method described above is carried out dopaminergic activity is produced. For an average size human for the preferred species (A) a preferred oral dose to show anti-hypertensive activity would be selected from the range of from about 100–250 mg for each dosage unit adapted for oral administration to be administered from 1–5 times daily.

The following examples are designed solely to illustrate the preparation and use of the compounds of this invention. The temperatures are Centigrade. Other variations of these examples will be obvious to those skilled in the art.

EXAMPLE 1

A mixture of 41.4 g (0.183 mole) of 2-allyl-3,4-dimethoxybenzyl chloride [R. Schwarz et al., Monatsh. 84 595 (1953)] and 210 ml of dimethylformamide was mixed with 10.5 g (0.214 mole) of sodium cyanide. The mixture was heated at 60° for 1.5 hours. Water (100 ml) was added until the solid present dissolved. The reaction mixture was then poured into 1 l. of water. The diluted reaction mixture was extracted twice with ether. The ether extract was backwashed with water, dried and evaporated to give 37.9 g. (75.6%) of oily 2-allyl-3,4-dimethoxyphenylacetonitrile. Nuclear magnetic resonance spectrum (NMR) checked.

The acetonitrile (15.25 g., 0.07 mole) in 100 ml of dry tetrahydrofuran was added dropwise over 20 minutes to a previously prepared solution of 3.15 g. (0.105 mole) of aluminum hydride in 140 ml. of dry tetrahydrofuran under argon. After stirring for 1.25 hours at ambient temperature, the mixture was worked up by adding sequentially 3.8 ml. of water, 3.8 ml. of 10% sodium hydroxide and 10 ml. of water. After separating the solid, the filtrate was evaporated to give 2-allyl-3,4-dimethoxy-β-phenethylamine as an oil. NMR checked.

A mixture of 12.7 g. (0.058 mole) of the phenethylamine and 11.3 g. (0.058 mole) of methyl 4-methoxymandelate was heated on a steam bath for 8 hours. The cooled reaction mixture was dissolved in ethyl acetate. The organic extract was then washed twice each with dilute hydrochloric acid and sodium bicarbonate solution. The dried organic extract was evaporated to give N-[2-(2-allyl-3,4-dimethoxyphenyl)ethyl]-4-methoxymandelamide, 20.6 g. (93%).

A commercial mixture of sodium bis(2-methoxyethoxy)aluminum hydride in toluene (60 ml., 0.23 mole) was added dropwise over a 1 hour period to a solution of the mandelamide (20.6 g.) in 180 ml. of toluene. The reaction mixture was heated at reflux for 1.5 hours then quenched carefully with 20 ml. of water. The solution was filtered and the filtrate evaporated. The residue was dissolved in methylene chloride. The organic extract was then shaken with dilute hydrochloric acid and sodium carbonate solution. The dried methylene chloride extract was evaporated to leave a residue which was passed over a silica column using 5% methanol-chloroform to give 8.2 g. (39%) of oily N-[2-hydroxy-2-(4-methoxyphenyl)-ethyl]-N-[2-(2-allyl-3,4-dimethoxyphenyl)ethyl]amine as the oily base.

Key NMR absorption (CDCl$_3$): 2.72 (m, 6, —CH$_2$CH$_2$NHCH$_2$—).

A mixture of 4.5 g. (0.012 mole) of the secondary amine and 34 ml. of cold trifluoroacetic acid was prepared. After adding 0.97 ml. of conc. sulfuric acid, the reaction mixture was stirred at ambient temperature for 60 hours. Anhydrous sodium acetate (1.5 g., 1 eq.) was added. Stirring was continued until the salt dissolved. The organic solvent was evaporated. The residue was partitioned between ethyl acetate and 10% sodium hydroxide solution. After extracting the alkali layer with ethyl acetate, the combined organic extracts were dried and evaporated. The residue was extracted with ether. The ethereal extract was dried and treated with ethereal hydrogen chloride to separate, after chromatographic purification over silica with 10% methanol chloroform, 1.37 g. (30%) of 8-methoxy-1-(4-methoxyphenyl)-6,7-(2-methyl-2,3-dihydrofuro)-2,3,4,5-tetrahydro-1H-3-benzazepine hydrochloride, m.p. 236°–239°.

C$_{21}$H$_{24}$NO$_3$.HCl.½H$_2$O Anal. Calcd: C, 65.53; H, 7.07; N, 3.65 Found: C, 65.17; H, 7.16; N, 3.53

Key NMR absorption (CDCl$_3$): 2.75 (m, 6, CH$_2$NHCH$_2$, ArCH$_2$CH); 4.93 (m,1,

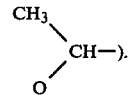

EXAMPLE 2

A mixture of 2.8 g. (0.0083 mole) of the dimethoxy product of Example 1 in 50 ml. of methylene chloride was cooled to −15° at which temperature 10 ml. of boron tribromide was added dropwise. A red precipitate formed but dissolved as the mixture was stirred at ambient temperature for 3 hours. The mixture was cooled to −15°. A 1:1 mixture of methanol and methylene chloride was added to destroy excess boron tribromide. The solvents are evaporated. The residue was recrystallized from ethyl acetate-ether to give 1 g. of crude 8-hydroxy-1-(4-hydroxyphenyl)-6,7-(2-methyl-2,3-dihydrofuro)-2,3,4,5-tetrahydro-1H-3-benzazepine hydrobromide. A sample was recrystallized from methanolethyl acetate then water to give an analytical sample, m.p. 317°.

$C_{19}H_{20}NO_3 \cdot HBr \cdot \frac{1}{4}H_2O$ Anal. Calcd: C, 57.51; H, 5.27; N, 3.53 Found: C, 57.73; H, 5.72; N, 3.74

NMR and mass spectrum consistant.

The hydrobromide salt (500 mg.) is neutralized by shaking in sodium carbonate solution-ether. The dried ether extract is divided into aliquots. One is evaporated to give the free base. The other is reacted with an excess of methan sulfonic acid in ispopropanol to give the methane sulfonic acid salt.

EXAMPLE 3

A mixture of 5.6 g (0.016 mole) of 8-methoxy-1-(4-methoxyphenyl)-6,7-(2-methyl-2,3-dihydrofuro)-2,3,4,5-tetrahydro-1H-3-benzazepine and 75 ml. of acetonitrile is mixed with 3.0 ml. of triethylamine and 2.2 ml. of allyl bromide. The mixture is heated on the steam bath for 3 hours then evaporated. The residue is suspended in water and extracted twice with ethyl acetate. The extracts are combined, washed with water then brine, dried and evaporated to give 3-allyl-8-methoxy-1-(4-methoxyphenyl)-6,7-(2-methyl-2,3-dihydrofuro)-2,3,4,5-tetrahydro-1H-3-benzazepine as the base.

The hydrochloride salt is prepared by treating 300 mg. of the 3-allyl base in methanol with ethereal hydrogen chloride.

The remainder of the base (2.7 g.) is dissolved in 55 ml. of methylene chloride, then cooled to $-15°$ at which temperature 6 ml. of boron tribromide in methylene chloride is added at that temperature dropwise. After stirring at room temperature overnight, the reaction mixture is mixed with methanol and evaporated. Methanol-ethyl acetate treatment gives 3-allyl-6,7-(2-methyl-2,3-dihydrofuro)-8-hydroxy-1-(4-hydroxyphenyl)-2,3,4,5-tetrahydro-1H-3-benzazepine hydrobromide.

EXAMPLE 4

A mixture of 25.4 g. (0.116 mole) of 2-allyl-3,4-dimethoxy-β-phenethylamine and 22 g. of methyl mandelate is heated on a steam bath for 5 hours. The mixture is worked up as described in Example 1 to give N-[2-(2-allyl-3,4-dimethoxyphenyl)ethyl]mandelamide. This material (40 g.) is reduced with an excess of sodium bis(2-methoxyethoxy)aluminum hydride in toluene first at room temperature then at reflux. Working up gives N-(2-hydroxy-2-phenylethyl)-N-[2-(2-allyl-3,4-dimethoxyphenyl)ethyl]amine. This compound (6.8 g.) is combined with 50 ml. of cold trifluoroacetic acid then 1.3 ml. of concentrated sulfuric acid. The mixture is stirred at room temperature for 2 days. Working up as described gives 8-methoxy-6,7-(2-methyl-2,3-dihydrofuro)-1-phenyl-2,3,4,5-tetrahydro-1H-3-benzazepine as the base. Treating 1.2 g. of the 8-methoxy compound with an excess of boron tribromide in methylene chloride first at $-20°$ then at room temperature for 5 hours gives the desired product 8-hydroxy-6,7-(2-methyl-2,3-dihydrofuro)-1-phenyl-2,3,4,5-tetrahydro-1H-3-benzazepine hydrobromide.

EXAMPLE 5

A mixture of 3.5 g. of 8-methoxy-6,7-(2-methyl-2,3-dihydrofuro)-1phenyl-2,3,4,5-tetrahydro-1H-3-benzazepine (prepared as in Example 4), 15 ml. of formic acid and 10 ml. of formaldehyde is heated at reflux for 24 hours. The reaction mixture is evaporated to dryness. 6 N Hydrochloric acid (20 ml.) is added to the residue and the mixture is again evaporated. The residue is treated with 20 ml. of 10% sodium hydroxide solution. The mixture is extracted with ether. After drying and evaporation of the ether extract, 8-methoxy-3-methyl-6,7-(2-methyl-2,3-dihydrofuro)-1-phenyl-2,3,4,5tetrahydro-1H-3-benzazepine hydrochloride is recovered. Treatment with boron tribromide as in Example 4 gives the 8-hydroxy congener as the base and as the hydrobromide.

EXAMPLE 6

3-Allyl-8-dihydroxy-1-(4-hydroxyphenyl)-6,7-(2-methyl-2,3-dihydrofuro)-2,3,4,5-tetrahydro-1H-3-benzazepine hydrobromide (1.0 g.) is slurried in 200 ml. of trifluoroacetic acid then 1.29 ml. of acetyl bromide is added. The mixture is heated at reflux for 2 hours then stirred for 2 hours. After evaporation to dryness the residue is taken up in benzene and concentrated to give 3-allyl-8-acetoxy-1-(4-acetoxyphenyl-6,7-(2-methyl-3,4-dihydrofuro)-2,3,4,5-tetrahydro-1H-3-benzazepine hydrobromide.

Similarly the isobutyryloxy, propionyloxy, isovaleryloxy, n-butyryloxy, n-heptanoyloxy and other higher derivatives are prepared at the 8-hydroxy or the phenyl hydroxy groups.

EXAMPLE 7

Using the reaction and isolation methods of Examples 1 and 2:

A. 2-allyl-3,4-dimethoxy-β-phenethylamine and methyl 2-fluoromandelate give N-[2-(2-allyl-3,4-dimethoxyphenyl)ethyl]2-fluoromandelamide, N-(2-hydroxy-2-fluorophenylethyl)-N-[2-(2-allyl-3,4-dimethoxyphenyl)ethyl]amine, 1-(2-fluorophenyl)-8-methoxy-6,7-(2-methyl-2,3-dihydrofuro)-2,3,4,5-tetrahydro-1H-3-benzazepine and 1-(2-fluorophenyl)-8-hydroxy-6,7-(2-methyl-2,3-dihydrofuro)-2,3,4,5-tetrahydro-1H-3-benzazepine together with its hydrobromide salt.

B. 2-allyl-3,4-dimethoxy-β-phenethylamine and ethyl 3-methylmandelamide give N-[2-(2-allyl-3,4-dimethoxyphenyl)ethyl] 3-methylmandelamide, N-(2-hydroxy-2,3-methylphenylethyl)-N-[2-(2-allyl-3,4-dimethoxyphenyl)ethyl]amine, 1-(3-methylphenyl)-8-methoxy-6,7-(2-methyl-2,3-dihydrofuro)-2,3,4,5-tetrahydro-1H-3-benzazepine, 1-(3-methylphenyl)-8-hydroxy-6,7-(2-methyl-2,3-dihydrofuro)-2,3,4,5-tetrahydro-1H-3-benzazepine together with its hydrochloric salt.

C. 2-allyl-3,4-dimethoxy-β-phenethylamine and ethyl 4-trifluoromethylmandelate give N-[2-(2-allyl-3,4-dimethoxyphenyl)ethyl]4-trifluoromethylmandelate, N-(2-hydroxy-2-4-trifluoromethylphenylethyl)-N-[2-(2-allyl-3,4-dimethoxyphenyl)ethyl]amine, 8-methoxy-6,7-(2-methyl-2,3-dihydrofuro)-1-(4-trifluoromethylphenyl)-2,3,4,5-tetrahydro-1H-3-benzazepine and 8-hydroxy-6,7-(2-methyl-2,3-dihydrofuro)-1-(4-trifluoromethylphenyl)-2,3,4,5-tetrahydro-1H-3-benzazepine together with its sulfate salt.

D. 2-allyl-3,4-dimethoxy-β-phenethylamine and methyl 4-chloromandelate gives N-[2-(2-allyl-3,4-dimethoxyphenyl)ethyl]4-chloromandelate, N-(2-hydroxy-2-4-chloro phenylethyl)-N-[2-(2-allyl-3,4-dimethoxyphenyl)ethyl]amine, 1-(4-chlorophenyl-8-methoxy-6,7-(2-methyl-2,3-dihydrofuro)-2,3,4,5-tetrahydro-1H-3-benzazepine and 1-(4-chlorophenyl)-8-hydroxy-6,7-(2-methyl-2,3-dihydrofuro)-2,3,4,5-tetrahydro-1H-3-benzazepine together with its hydrobromide salt.

E. 2-allyl-3,4-dimethoxy-β-phenethylamine and methyl 4-methylthiomandelate give N-[2-(2-allyl-3,4-dimethoxyphenyl)ethyl]4-methylthiomandelate, N-(2- hydroxy-2-4-methylthiophenylethyl)-N-[2-(2-allyl-3,4-dimethoxyphenyl)ethyl]amine, 8-methoxy-6,7-(2-methyl-2,3-dihydrofuro)-1-(4-methylthiophenyl)-2,3,4,5-tetrahydro-1H-3-benzazepine and 8-hydroxy-6,7-(2-methyl-2,3-dihydrofuro)-1-(4-methylthiophenyl)-2,3,4,5-tetrahydro-1H-3-benzazepine as its hydrobromide salt.

EXAMPLE 8

| Ingredients | Mg. per Capsule |
| --- | --- |
| 8-Hydroxy-1-(4-hydroxyphenyl)-6,7-(2-methyl-2,3-dihydrofuro)-2,3,4,5-tetrahydro-1H-3-benzazepine methane sulfonic acid salt | 150 (free base) |
| Magnesium stearate | 2 |
| Lactose | 200 |

The ingredients are thoroughly mixed and placed into hard gelatin capsules. One capsule is administered orally to patients in need of peripheral dopaminergic activity from 1–5 times daily.

What is claimed is:

1. A compound of the structural formula:

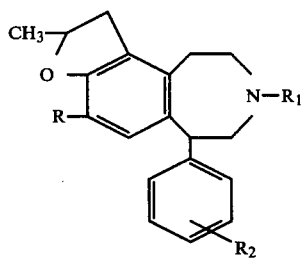

in which R is hydroxy or methoxy, $R_1$ is hydrogen, methyl or allyl and $R_2$ is hydrogen, methoxy, hydroxy, methyl, methylthio, trifluoromethyl or halo; together with a pharmaceutically acceptable acid addition salt or O-lower alkanoyl ester thereof.

2. The compound of claim 1 being 8-hydroxy-1-(4-hydroxyphenyl)-6,7-(2-methyl-2,3,-dihydrofuro)-2,3,4,5-tetrahydro-1H-3-benzazepine or a pharmaceutically acceptable acid addition salt thereof.

3. The compound of claim 1 being 8-hydroxy-1-(4-hydroxyphenyl)-6,7-(2-methyl-2,3-dihydrofuro)-2,3,4,5-tetrahydro-1H-3-benzazepine methane sulfonate salt.

4. The compound of claim 1 being 8-hydroxy-1-(4-hydroxyphenyl)-6,7-(2-methyl-2,3-dihydrofuro)-2,3,4,5-tetrahydro-1H-3-benzazepine as the free base.

5. The compound of claim 1 being 8-methoxy-1-(4-methoxyphenyl)-6,7-(2-methyl-2,3-dihydrofuro)-2,3,4,5-tetrahydro-1H-3-benzazepine or a pharmaceutically acceptable acid addition salt thereof.

6. The compound of claim 1 being 3-allyl-8-hydroxy-1-(4-hydroxyphenyl)-6,7-(2-methyl-2,3-dihydrofuro)-2,3,4,5-tetrahydro-1H-3-benzazepine or a pharmaceutically acceptable acid addition salt thereof.

7. The method of inducing peripheral dopaminergic activity in a subject in need thereof comprising administering orally or parenterally thereto a nontoxic dopaminergic quantity of a compound of claims 1, 2, 3, 4, 5 or 6.

8. The pharmaceutical composition having peripheral dopaminergic activity comprising a nontoxic dopaminergic quantity of a compound of claims 1, 2, 3, 4, 5 or 6 combined with a pharmaceutical carrier.

9. The method of preparing a compound of the formula:

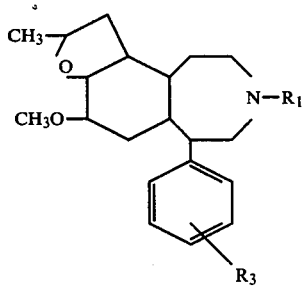

in which $R_1$ is hydrogen, methyl or allyl and $R_3$ is hydrogen, methoxy, methyl, methylthio, trifluoromethyl or halo, comprising reacting a compound of the formula:

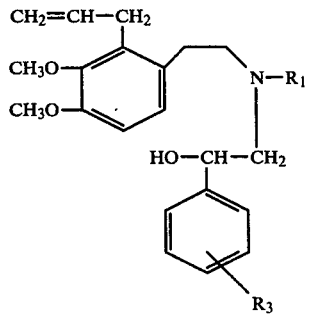

in which $R_1$ and $R_3$ are as defined above, in the presence of sulfuric acid-trifluoroacetic acid at ambient temperature until reaction is complete.

* * * * *